United States Patent [19]

Bacon, Jr.

[11] Patent Number: 5,234,838
[45] Date of Patent: Aug. 10, 1993

[54] AMMONIA MONITOR BASED ON ION MOBILITY SPECTROMETRY WITH SELECTIVE DOPANT CHEMISTRY

[75] Inventor: Allan T. Bacon, Jr., Joppatowne, Md.

[73] Assignee: Environmental Technologies Group, Inc., Baltimore, Md.

[21] Appl. No.: 746,464

[22] Filed: Aug. 16, 1991

Related U.S. Application Data

[63] Continuation-in-part of Ser. No. 687,594, Apr. 17, 1990, Pat. No. 5,095,206, which is a continuation-in-part of Ser. No. 534,701, Jun. 1, 1990, Pat. No. 5,032,721.

[51] Int. Cl.$^5$ ............................................. G01N 24/00
[52] U.S. Cl. ..................................... 436/173; 436/113; 436/171; 422/82.01; 422/82.02; 422/90; 422/98; 250/282; 250/286; 250/287; 250/288
[58] Field of Search ................ 436/113, 171, 173; 422/82.05, 82.01, 82.02, 83, 90, 98; 250/282, 286, 287, 288

[56] References Cited

U.S. PATENT DOCUMENTS

| | | | |
|---|---|---|---|
| 3,717,028 | 2/1973 | Annino et al. | 73/23.36 |
| 4,374,090 | 2/1983 | McClure | 422/98 |
| 4,378,499 | 3/1983 | Spangler et al. | 250/287 |
| 4,445,038 | 4/1984 | Spangler et al. | 250/287 X |
| 4,551,624 | 11/1985 | Spangler et al. | 422/98 X |
| 4,712,008 | 12/1987 | Vora et al. | 250/287 |
| 4,777,363 | 10/1988 | Eiceman et al. | 250/287 X |
| 4,950,893 | 8/1990 | Reategui et al. | 250/282 |
| 5,032,721 | 7/1991 | Bacon et al. | 250/282 |
| 5,095,206 | 3/1992 | Bacon, Jr. et al. | 250/282 |

Primary Examiner—James C. Housel
Assistant Examiner—Maureen M. Wallenhorst
Attorney, Agent, or Firm—Leonard Bloom

[57] ABSTRACT

An improved ion mobility spectrometer (IMS) and method for operating the same which enables analysis of ammonia in a mixture of gases when air is used as the carrier gas and the drift gas in the IMS. A controlled concentration of an ester such as Dimethyl methyl phosphonate (DMMP) is added to the air carrier gas stream prior to application of the carrier gas stream. The DMMP clusters with the ammonia, and the drift times of the ionized clusters differ from the drift times of the ions generated from the other constituents of the sample, thereby enabling identification and quantification of the ammonia.

30 Claims, 3 Drawing Sheets

AMMONIA MONITOR BASED ON ION MOBILITY SPECTROMETRY WITH SELECTIVE DOPANT CHEMISTRY

CROSS-REFERENCE TO RELATED APPLICATIONS

This application is a continuation-in-part of application Ser. No. 687,594, filed Apr. 17, 1990, now U.S. Pat. No. 5,095,206 issued Mar. 10, 1992 which is a continuation-in-part of application Ser. No. 534,701, filed Jun. 1, 1990 now U.S. Pat. No. 5,032,721 issued Jul. 16, 1991.

FIELD OF THE INVENTION

The present invention relates to ion mobility spectrometry with improved specificity to certain gasses, and more particularly, to the use of an ester dopant and related improvements which enhance the specificity of detection of ammonia and amines.

BACKGROUND OF THE INVENTION

There is a fast growing commercial demand for monitoring systems capable of identifying and quantifying constituent gasses in a sample. The demand arises from the need to insure the purity of substances during the production process, and from the need to prevent hazardous gasses from escaping into the air. Monitoring in the latter context is becoming even more urgent as governments worldwide enact clean air regulations which limit the emissions of hazardous gasses from processing plants and storage facilities. The regulations compel the use of a monitor to enable corrective action in case the concentration of hazardous gas exceeds a specified level, and to provide an early warning of impending danger to plant personnel and the public.

Efforts to satisfy the commercial demand have resulted in a wide variety of monitors each dedicated to sensing different gasses in different environments. For instance, a frequent need arises to analyze ammonia. Ammonia is a toxic and flammable substance widely used in many manufacturing and chemical processes. In addition, it is a prime ingredient in the widespread process known as de-NOx. More specifically, in any open-air burning, compounds comprising oxides of nitrogen (NOx) are produced. The NOx poses a significant health hazard and contributes to acid rain, hence the emission rate is strictly regulated. To remove the NOx, ammonia is introduced in the exhaust stream, and the stream is passed over a catalyst. The NOx is removed by reaction with the ammonia and non-toxic byproducts are exhausted. Unfortunately, the de-NOx process is extremely difficult to control, and significant amounts of ammonia may escape through the exhaust smokestack.

In addition to de-NOx, unwelcome ammonia may also appear in certain process streams, for example, in the processing of ethylene. In order to purify the ethylene, trace amounts of ammonia concentration must be accurately measured.

Ideally, an ammonia monitor suited for the above-described analysis of ammonia should operate continuously over extended periods of time without the need for frequent maintenance or calibration. Current monitoring systems use electrochemical sensors, spectroscopy, and related devices. These systems are generally inadequate because they lack specificity, require frequent maintenance, calibration, or replenishment of electrolyte. The electrolytic systems are limited to operating at ambient temperatures above 0° C. (due to freezing of the electrolyte).

In contrast, an Ion Mobility Spectrometer (IMS) is a well-known analytical tool capable of accurate and trouble-free analysis of the constituents in a sample. Basically, an IMS comprises an analyzer cell, means for ionizing samples of an analyte admitted to the cell and means for determining the times required for the ions of the various substances present in the cell to traverse a specific length of the cell under the influence of an electric field and against the force of a stream of drift gas flowing through the cell in a direction opposite to that of the electric field. A representative analyzer cell is disclosed in U.S. Pat. No. 4,390,784 issued to Browning, et al. A stream of purified gas may be used as a carrier gas to introduce the analyte sample into the cell, and a stream of purified gas may also be used as the drift gas. If the carrier gas and the drift gas are readily available at an installation site in unlimited quantities, then there is no maintenance required of the sensor other than the occasional replacement of filters and membranes for purifying the carrier and drift gasses, radiation wipe tests and calibration. An IMS is therefore well-suited for use in a monitoring system designed to detect and quantify hazardous gasses.

Unfortunately, it has been found that an IMS operated in a conventional manner, using air as the carrier and drift gasses, may lack the specificity necessary to detect ammonia under certain conditions. The conditions arise when interferants are present in the sample. For instance, in the de-NOx process there are hydrocarbons. In processes involving ethylene, the ethylene itself acts as an interferant. This is because interferants (such as hydrocarbons and ethylene) disrupt the ammonia peak. Hence, it becomes very difficult to distinguish the amplitude of the ion current due to the ammonia gas from the ion current due to the other sample constituents.

In application Ser. No. 534,701, now U.S. Pat. No. 5,032,721 issued Jul. 16, 1991 a monitor is disclosed which uses a dopant to improve the specificity for acid gasses. The dopant is selected from the group of substituted phenols, and improves the ability of the gas monitor to detect the general presence of acid gasses such as hydrogen fluoride, hydrogen chloride, chlorine, nitrogen dioxide, sulfur dioxide, carbonyl sulfide, and numerous others. This ability to improve IMS specificity for detection of acid gas is a significant refinement, but it does nothing to improve the specificity of detection for ammonia.

Likewise, the use of a dopant was disclosed in application Ser. No. 687,594 for improving the IMS specificity toward acid gases in air. The higher specificity is achieved by introducing a controlled concentration of sulfur dioxide dopant to the air carrier gas stream. The reaction with the acid gas causes the drift times of the ions generated from the doped air carrier gas to differ from the drift times of the ions generated from the acid gas analyte, thereby allowing identification and quantification of the acid gas analyte. This dopant chemistry is also advantageous for the detection of acid gasses, but cannot improve the specificity of detection for ammonia.

SUMMARY OF THE INVENTION

It is, therefore, an object of the present invention to provide a method of ion mobility spectrometry with improved specificity for detecting ammonia in a sample containing other constituents, whereby interference and false indications resulting from the other constituents are eliminated.

It is a specific object of the present invention to provide a method and apparatus based on ion mobility spectrometry which elevates the charge affinity of ammonia in a sample in order to improve the degree of specificity for ammonia in the sample containing ethylene.

It is a further object of the invention to accomplish the above described advantages for samples consisting primarily of ambient air or ethylene. According to the present invention, the above-described and other objects are accomplished by providing an ion mobility spectrometer with improved specificity for detecting ammonia in the presence of interferants. The spectrometer generally includes an analyzer cell having an inlet region, a reaction region, an ionization source in said reaction region, means for introducing a dopant into the reaction region, a shutter grid, a drift region, an ion current detector for detecting ions transiting said cell drift region, and means for measuring the transit times through the cell drift region of ions generated in the cell reaction region and released into the drift region through the shutter grid. The method of operation includes the steps of applying a drift gas stream of air to the cell drift region, mixing an ester with a carrier gas stream of air to create a doped carrier gas stream, introducing a test sample into the analyzer cell inlet region, applying the carrier gas stream to the cell inlet region to carry the test sample into the cell reaction region, and measuring an ion current at the ion current detector at a time corresponding to the transit time through the cell drift region of ions generated by the test sample in the cell reaction region. The ester forms an ion cluster with any ammonia in the sample to yield a product with a higher charge affinity. Hence ions generated by said carrier gas stream in the cell reaction region have transit times through said cell drift region which are different from the transit times through the cell drift region of ions generated by the test sample. At the same time, the dopant suppresses ion current attributable to interferants with low charge affinities. Consequently, the ester dopant improves the selectivity of the ion mobility spectrometer.

BRIEF DESCRIPTION OF THE DRAWINGS

Other objects, features and advantages of the present invention will become more apparent from the following detailed description of preferred embodiments and certain modifications thereof when taken together with the accompanying drawings, in which.

DETAILED DESCRIPTION OF THE PREFERRED EMBODIMENT(S)

Figure 1:
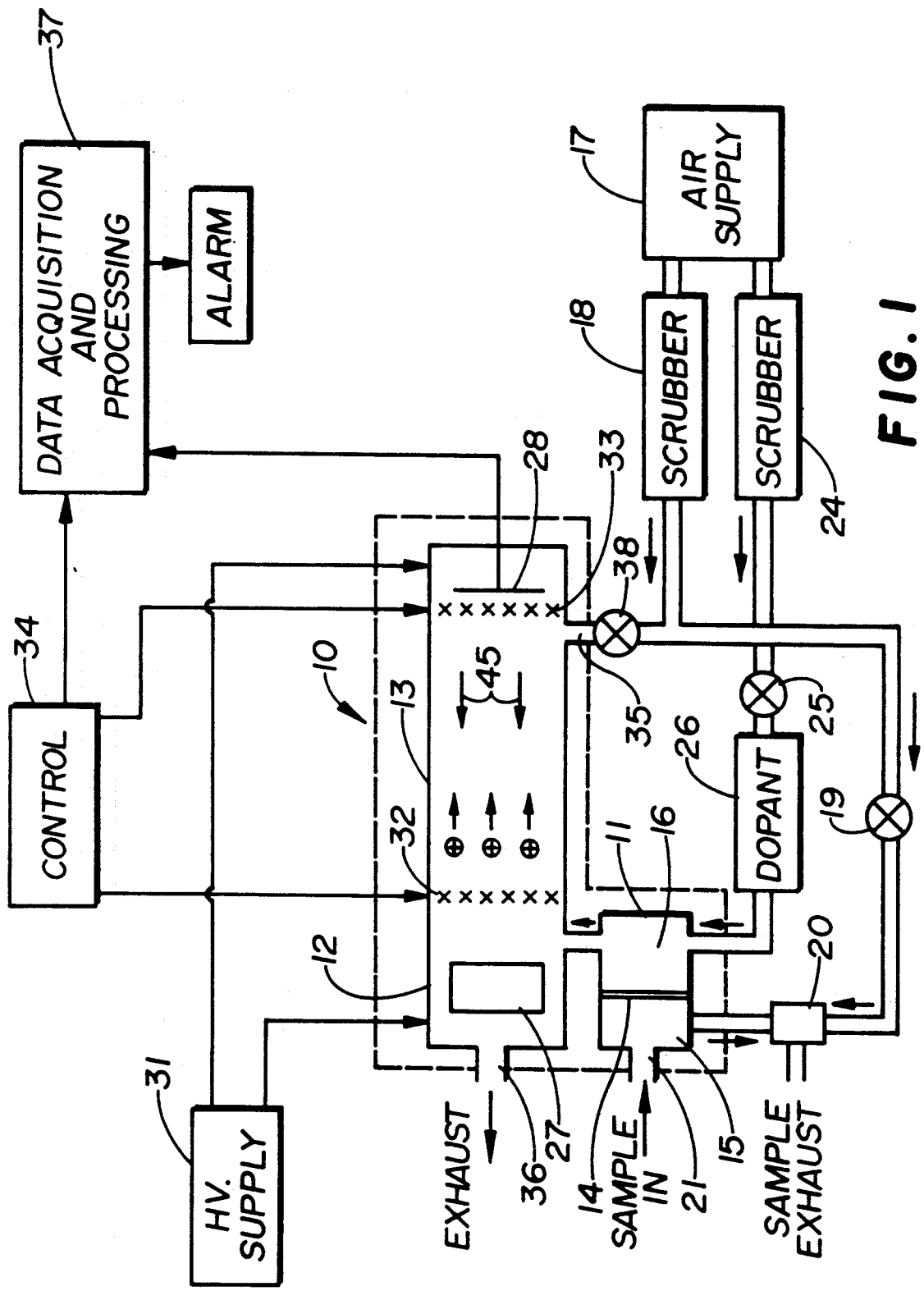
FIG. 1 is a functional block diagram of an Ion Mobility Spectrometer according to the present invention.

Referring to FIG. 1, the apparatus of the present invention comprises an IMS analyzer cell 10 similar to that disclosed in U.S. Pat. No. 4,390,784 issued to Browning, et al, with certain improvements to be described.

Cell 10 is divided into an inlet region 11, a reaction region 12 and a drift region 13. Inlet region 11 is partitioned by a permeable membrane 14 into a sample chamber 15 and an inlet chamber 16. Air from a regulated pressure air supply 17 is passed through a scrubber 18, flow regulator 19 and venturi 20 to an exhaust. The air flow through venturi 20 inducts a sample of gas into sample chamber 15 and through membrane 14. In the preferred embodiment, membrane 14 comprises a 0.001 inch diaphragm of microporous Teflon TM.

The inlet is inducted through membrane 14 and into sample chamber 16. The temperature of inlet chamber 16 is preferably maintained by a thermostat to insure a constant concentration of sample constituents.

The constituents passing through membrane 14 into chamber 16 are then swept from chamber 16 by a carrier gas into the reaction region 12 of analyzer cell 10.

In the preferred embodiment, the carrier gas stream comprises air from air supply 17 that is passed through a scrubber 24 primarily to remove water vapor therefrom, and through flow regulator 25. Alternatively, nitrogen and many other inert gasses may be used in place of air provided that the dew point is below $-40°$ F. This constraint is useful when sampling flammable mixtures.

Before it reaches the inlet region 11, the carrier gas stream is passed through a temperature-controlled permeation tube 26, where a controlled concentration of dopant is added to the air stream. The temperature of the permeation tube is preferably maintained by a thermostat to insure a constant flow of dopant.

It is essential to the present invention that the dopant form an ion cluster with ammonia in the test sample. This improves the specificity to ammonia because the product ions generated by the ammonia clusters have a higher charge affinity than ammonia alone. Several compounds from among the class of compounds known as esters will form clusters with ammonia, and hence may be used in the present invention. Esters of phosphoric acid, and more specifically, phosphonates exhibit the best clustering. Therefore, dimethyl methyl phosphonate (DMMP) is used in the preferred embodiment of the invention.

Reaction region 12 contains an ionization source 27 which generates product ions from the constituents swept into region 12 by the carrier gas. Source 27 may be of the $\beta$-particle ionizing radiation type which is usually formed of a ring of Ni63. Alternatively, source 27 may be one of a variety of sources known in the field, such as ultraviolet, corona discharge, thermionic, etc.

The product ions formed in region 12 are driven in the direction of an ion detector 28, located at the end of drift region 13 opposite reaction region 12, by an electrostatic field generated along regions 12 and 13 by a high voltage supply 31. Reaction region 12 is partitioned from drift region 13 by a shutter grid 32, and ion detector 28 is separated from drift region 13 by an aperture grid 33. Shutter grid 32 and aperture grid 33 are separately biased by voltages from a control circuit 34. The drift gas, admitted to drift region 13 through port 35, flows continuously through drift region 13 and reaction region 12, exhausting therefrom through exhaust vent 36.

Preferably, the drift gas likewise comprises air from air supply 17 which is passed through scrubber 18 and flow regulator 38 into port 35. As with the carrier gas, nitrogen or several other inert gasses may be used in place of air provided that the gas has a dew point below −40° F. Like the carrier gas, the drift gas stream may also be passed through a temperature-controlled permeation tube (not shown) for the purpose of introducing a controlled concentration of dopant to the air stream.

The ion mobility spectrometer of the present invention should be operated in the positive mode to generate positive product ions at the source 27.

Shutter grid 32 is biased positively for the major part of a scan cycle to block the product ions in reaction region 12 from entering drift region 13. At the beginning of a scan period, the bias is changed briefly to allow a cloud of ions to enter drift region 13. The ions accelerate along the length of drift region 13 toward the detector 28 under the influence of the electric field and against the force of the counter-flowing drift gas (represented by the arrows 45). The product ions created by the various constituents traverse the drift region in different time periods, depending upon the charge/molecular size characteristics of each constituent. If a complete spectrum is to be taken, aperture grid 33 may be neutrally biased so that the arrival times of each of the various ion groups at detector 28 may be measured. If the IMS is intended to be responsive to only a single specific substance, the aperture grid may be biased so as to repel all ions except for those arriving at a time corresponding to the predetermined characteristic arrival time of ions for the substance of interest.

Alternatively, the IMS may be operated in the enhancement mode, as disclosed and claimed in U.S. Pat. No. 4,950,893 issued Aug. 21, 1990 to J. A. Reategui, et al. for "Method and Apparatus for Enhanced Ion Spectrum Generation and Detection in Ion Mobility Spectrometry", assigned to the assignee of the present application. Briefly, in the enhancement mode, the shutter grid 32 of the IMS is biased open for the major portion of a scan cycle allowing ions to enter drift region 13 continuously upon their generation in the cell reaction region 12. At the beginning of a scan cycle, the shutter grid 32 is momentarily biased closed, thereby creating a void in the otherwise continuous stream of ions transiting from reaction region 12 into drift region 13. The void traverses drift region 13 and becomes separated into secondary voids which arrive at ion detector 28 at different transit times, in much the same manner as the ion groups which traverse and become separated in the conventional mode. The substantially steady stream of ions that enters drift region 13 during the open period of the shutter grid establishes a baseline ion current at detector 28. The arrival of a secondary void at detector 28 creates a negative peak in the base line current. The arrival time at detector 28 of a negative peak characterizes the identity of one constituent substance of the test sample, and the amplitude of the negative peak characterizes the concentration of the constituent substance in the test sample. Operation of an IMS in the enhancement mode has the advantages of producing better resolution of the separated ion current peaks and of providing a means permitting continuous calibration of the IMS.

Figure 2:
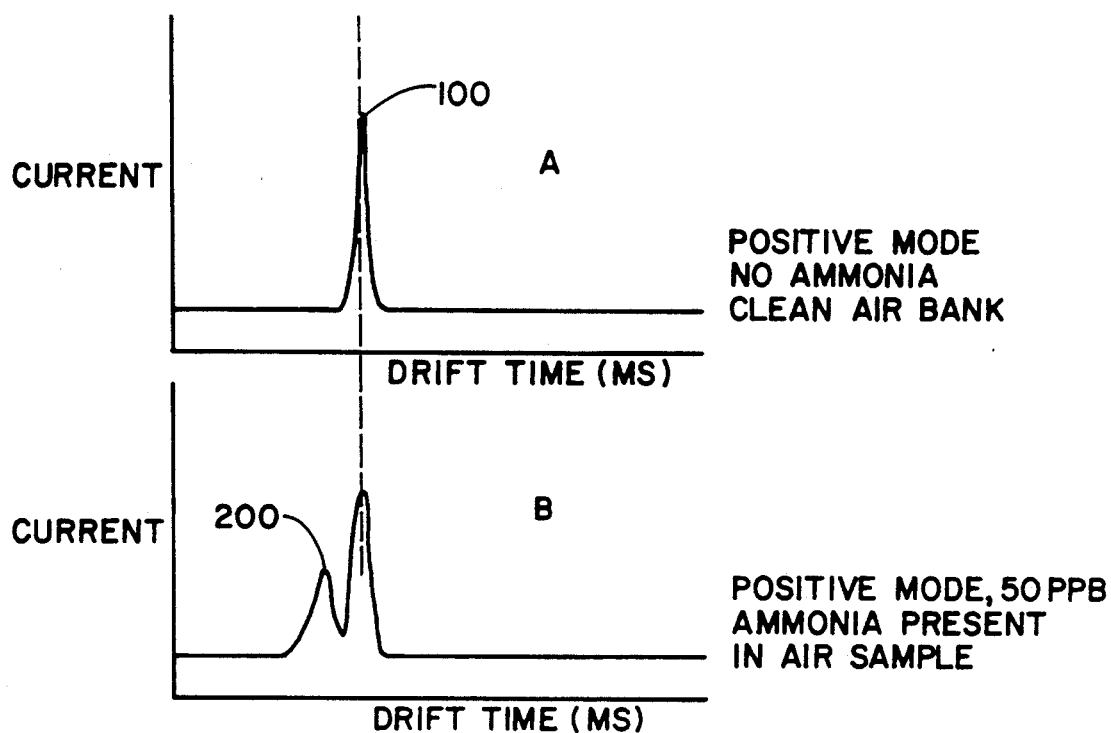
FIG. 2 is a comparative spectrograph showing the ion current peaks produced in the IMS of FIG. 1 by a test sample of air in which a trace amount of ammonia is/is not present. Purified air alone is used the carrier gas.

FIG. 2 is a comparative spectrograph showing the ion current peak produced when purified air alone is used as the carrier gas in an IMS operated in the positive mode. In graph A, no ammonia is present in the test sample. The ion current peak 100 appears at an arrival time of approximately 10.56 milliseconds (ms). Graph B of FIG. 2 shows the ion current peak produced when purified air alone is used as the carrier gas in the IMS and ammonia is present in the test sample in the amount of 50 parts per billion. The peak in graph B due to the ammonia occurs at approximately 9.5 milliseconds (ms). The proximity of the two peaks 100 and 200 makes it difficult to distinguish the ammonia in a sample of pure air when purified air alone is used as the carrier gas.

Figure 3:
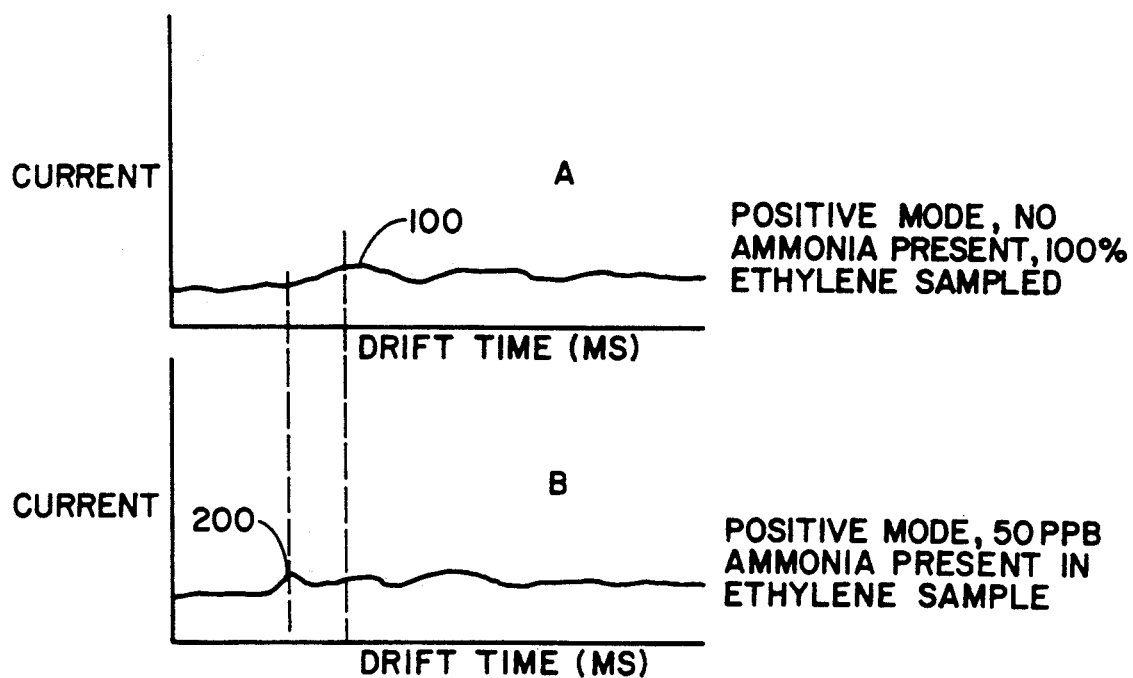
FIG. 3 is a comparative spectrograph showing the ion current peaks produced in the IMS of FIG. 1 by a test sample of ethylene in which a trace amount of ammonia is/is not present. Purified air alone is used the carrier gas.

FIG. 3 demonstrates the complete impracticality of distinguishing ammonia in a sample of ethylene when purified air alone is used as the carrier gas.

FIG. 3 is a comparative spectrograph showing the ion current peak produced by a sample of pure ethylene when purified air alone is used as the carrier gas in an IMS operated in the positive mode. In graph A, no ammonia is present in the test sample. The ion current peak 100 barely appears at an arrival time of approximately 10.56 milliseconds (ms). Graph B of FIG. 2 shows the effect when 50 parts per billion of ammonia is present in the test sample and purified air alone is used as the carrier gas. The peak 200 due to the ammonia occurs at approximately 9.5 milliseconds (ms). The ethylene peaks steal charge from the ion current peak produced by the ammonia. The resulting specificity is decreased to the point where the ammonia peak is barely detected. Thus, it becomes impossible to quantify the amount of ammonia.

The DMMP dopant administered in accordance with the present invention produces an ammonia cluster which has a higher charge affinity and different drift time. This eliminates or reduces the interference from ion peaks attributable to constituents having a lower charge affinity.

Figure 4:
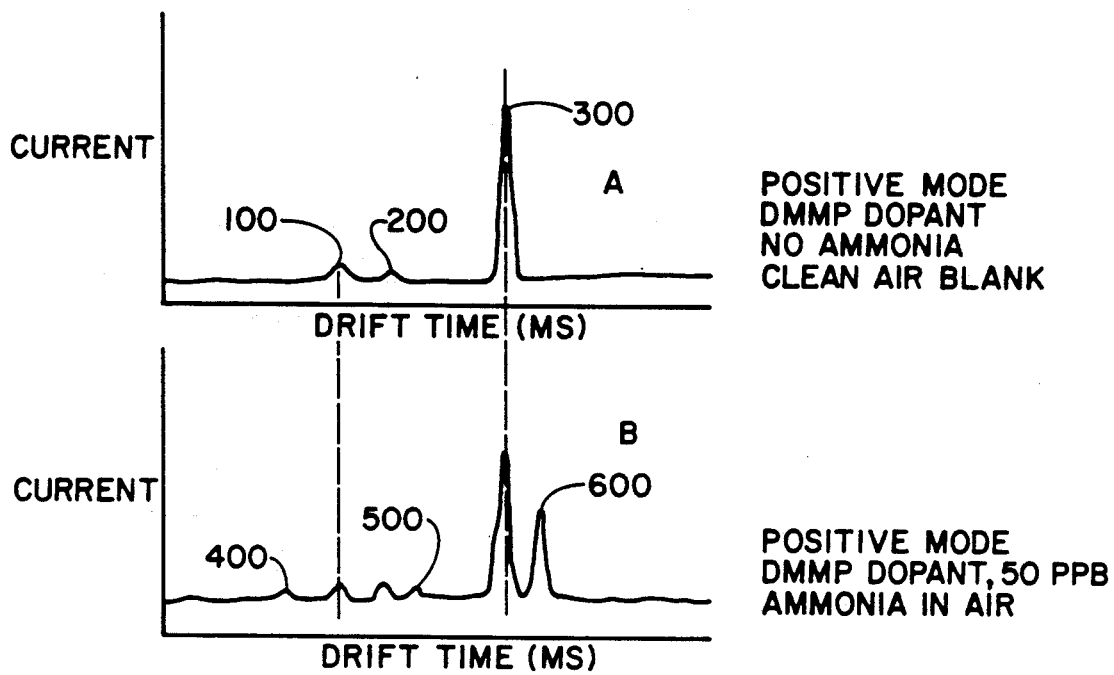
FIG. 4 is a comparative spectrograph showing the ion current peaks produced in the IMS of FIG. 1 by a test sample of air in which a trace amount of ammonia is/is not present. The IMS is operated in accordance with the present invention with an ester dopant introduced into the carrier gas stream of air.

FIG. 4 is a comparative spectrograph showing the ion current peaks produced by a sample of purified air when the DMMP dopant is introduced in the carrier gas and the IMS is operated in the positive mode. In graph A, no ammonia is present in the test sample, and the DMMP dopant does not cluster. Peak 100 (at approximately 10.9 ms) is due to the normal IMS reactant ion generated by the pure air sample. Peak 200 (at approximately 13.0 ms) is due to the DMMP monomer. Peak 300 (at approximately 16.6 ms) is due to the DMMP dimer.

Graph B of FIG. 4 shows the ion current peak produced when ammonia is present in the test sample in the amount of 50 parts per billion. Three additional peaks 400, 500 and 600 are generated as the result of clustering. Peak 400 (at approximately 10.1 ms) is due to the ammonia itself. Peak 500 (at approximately 13.0 ms) is due to the DMMP monomer/ammonia cluster. Peak 600 is due to the DMMP dimer/ammonia cluster. Peak 600 (at approximately 18.3 ms) is the peak of interest because it is clearly distinguishable from all other peaks. Hence, peak 600 clearly indicates the presence of ammonia in the sample. Moreover, the concentration of ammonia in the sample can be determined from the amplitude of the DMMP dimer/ammonia cluster peak.

The benefits of the DMMP dopant are even more apparent when the IMS is used to detect ammonia in ethylene.

Figure 5:
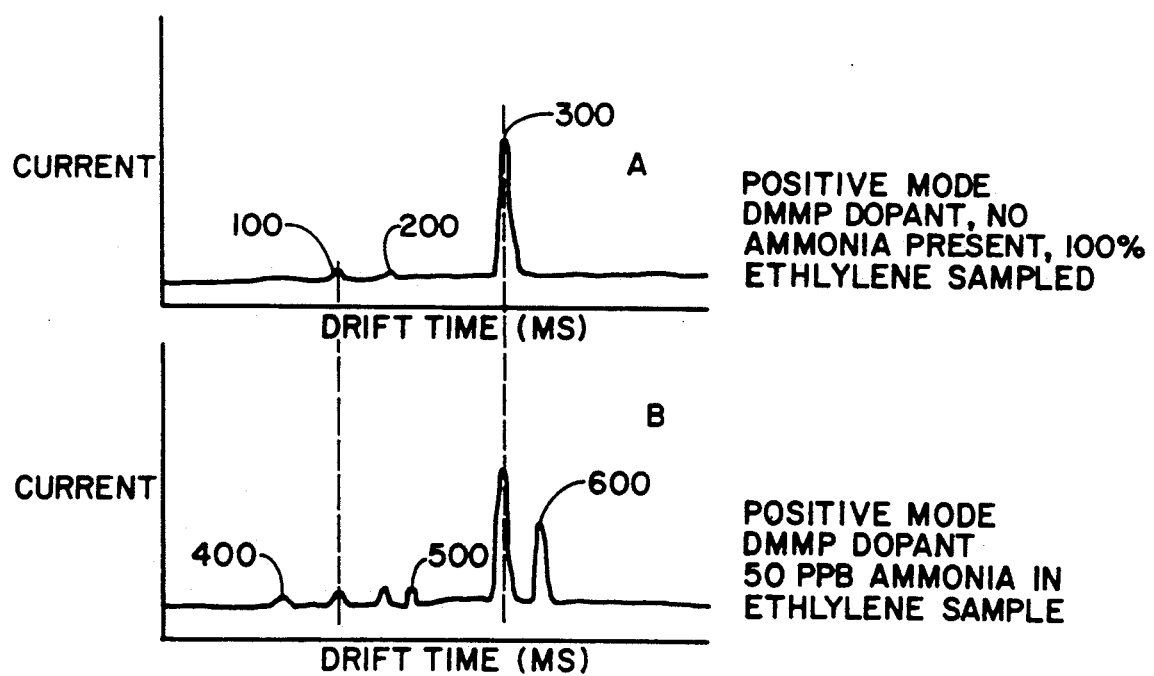
FIG. 5 is a comparative spectrograph showing the ion current peaks produced in the IMS of FIG. 1 by a test sample of ethylene in which a trace amount of ammonia is/is not present. The IMS is operated in accordance with the present invention with an ester dopant introduced into the carrier gas stream of air.

FIG. 5 is a comparative spectrograph showing the ion current peaks produced by a sample of ethylene when the DMMP dopant is introduced in the carrier gas and the IMS is operated in the positive mode. In graph A, no ammonia is present in the test sample, and the DMMP dopant does not cluster. Peak 100 (at approximately 10.9 ms) is due to the normal IMS reactant ion generated by the pure air sample. Peak 200 (at approximately 13.0 ms) is due to the DMMP monomer. Peak 300 (at approximately 16.6 ms) is due to the DMMP dimer.

Graph B of FIG. 5 shows the ion current peak produced when ammonia is present in the test sample in the amount of 50 parts per billion. The same three additional peaks 400, 500 and 600 are generated as the result of clustering. Peak 400 (at approximately 10.1 ms) is due to the ammonia itself. Peak 500 (at approximately 13.0 ms) is due to the DMMP monomer/ammonia cluster. Peak 600 (at approximately 18.3 ms) is due to the DMMP dimer/ammonia cluster. Peak 600 is clearly distinguishable from all other peaks, and once again, it can be used to quantify the concentration of ammonia in the sample of ethylene. This is in stark contrast to FIG. 3, in which the ammonia was completely indistinguishable.

The conditions under which the results of FIGS. 2–5 were obtained were as follows:
carrier gas flow—50 cc/min;
drift gas flow—100 cc/min;
carrier and drift gas—nitrogen (for increased safety)
inlet sample flow rate—200 cc/min.
inlet region temperature—50°;
cell temperature—50°;
operation—positive ion mode;
shutter grid pulse width—200 us;
inlet membrane—0.001 inch microporous teflon.
dopant flow rate into inlet region 16—365 nanograms per minute (resulting from permeating 1 part dopant per million carrier gas).

It should be noted that none of the above parameters are limiting, and that the invention can be practiced with wide deviations therefrom.

For instance, one skilled in the art would appreciate that different membranes are used to obtain different degrees of specificity and sensitivity, depending on the particular application.

The monitoring system described above requires less than 15 minutes for the average peak ion current to stabilize at an equilibrium level. In the preferred embodiment, the data is smoothed by taking a moving (or sliding) average of a plurality of peak heights measured during successive scans. Approximately 20 scans are completed, and the average is calculated from eight spectra. Peak height ratios are then calculated by dividing the height of peak 600 (due to the DMMP dimer/ammonia cluster) by the height of peak 300 (due to the DMMP dimer). The ratio is then compared to a look-up table to determine the ammonia concentration.

Having now fully set forth the preferred embodiment and certain modifications of the concept underlying the present invention, various other embodiments as well as certain variations and modifications of the embodiments herein described will obviously occur to those skilled in the art upon becoming familiar with said underlying concept. For example, the method and apparatus herein described may serve equally well in detecting compounds of the chemical class of amines, and other compounds which include nitrogen which have properties similar to ammonia. It is to be understood, therefore, that within the scope of the appended claims, the invention may be practiced otherwise than as specifically set forth herein.

What is claimed is:

1. A method for operating an ion mobility spectrometer to monitor ammonia in a test sample, the method comprising the steps of:
   introducing a test sample of gas into said ion mobility spectrometer;
   mixing an ester dopant with said test sample within said ion mobility spectrometer, said ester dopant forming clusters with the ammonia in said test sample when mixed therewith;
   applying said doped test sample to an ionization source;
   generating an ion current by ionization of said clusters at said ionization source; and
   measuring said ion current at a distance from said ionization source;
   whereby a peak ion current generated by said clusters is distinguishable from a peak ion current generated by other ionized constituents in the test sample because ions generated by said clusters travel said distance in a transit time which is characteristically different from the transmit time of ions generated by said other ionized constituents and computing a quantity of ammonia in said test sample based upon said peak in current generated by said clusters.

2. The method according to claim 1, whereby said step of mixing an ester dopant with said test sample suppresses ion current generated by test sample constituents having low charge affinities so that said measured ion current is attributable mainly to said clusters which have a higher charge affinity.

3. The method of claim 1, wherein said ester dopant comprises an ester of phosphoric acid.

4. The method of claim 3, wherein said ester of phosphoric acid is a phosphonate.

5. The method of claim 4, wherein said phosphonate is dimethyl methyl phosphonate (DMMP).

6. The method of claim 5, wherein said ion mobility spectrometer employs a carrier gas in transporting said test sample to said ionization source, and said step of mixing said DMMP dopant further comprises mixing said DMMP dopant with said carrier gas stream of air and applying the doped carrier gas stream to carry said test sample to said ionization source.

7. The method of claim 6, wherein said step of mixing said DMMP in said carrier gas stream comprises mixing said DMMP at a concentration of approximately 1 part per million.

8. The method of claim 6, wherein said step of mixing DMMP dopant with said carrier gas stream of air is accomplished by flowing said DMMP into a permeation tube immersed in said carrier gas stream, whereby said carrier gas mixes with DMMP permeating through said tube.

9. The method of claim 8, wherein said permeation tube is maintained at a constant temperature to preserve a uniform concentration of dopant.

10. The method of claim 5, wherein said step of mixing said DMMP dopant further comprises mixing said DMMP dopant with a drift gas stream of air and applying said drift gas stream to said test sample at said ionization source.

11. The method of claim 10, wherein said step of mixing said DMMP in said drift gas stream comprises mixing said DMMP at a concentration of approximately 1 part per million.

12. The method of claim 11, wherein said step of mixing DMMP dopant with said drift gas stream of air is accomplished by flowing said DMMP into a permeation tube immersed in said drift gas stream, whereby said drift gas mixes with DMMP permeating through said tube.

13. The method of claim 12, wherein said permeation tube is maintained at a constant temperature to preserve a uniform concentration of dopant.

14. The method of claim 1, wherein said ion mobility spectrometer is operated in a positive ion mode.

15. An ion mobility spectrometer for analyzing ammonia in a test sample, comprising:
an inlet region for inputting a test sample of gas;
a reaction region in fluid communication with said inlet region;
a source of ester dopant
doping means in fluid communication with said inlet region for applying said ester dopant to said test sample, said ester dopant forming clusters with ammonia in said test sample when mixed therewith;
an ionization source in said reaction region for generating product ions from the doped test sample;
a drift region through which said product ions travel in accordance with a charge and molecular size characteristic;
an ion current detector for detecting product ions transiting said drift region;
means for measuring an ion current detected by said ion current detector, whereby a peak ion current generated by said clusters is distinguishable from a peak ion current generated by other ionized constituents in said test sample because ions generated by said clusters have a transit time across said drift region which is characteristically different from the transit time of ions generated by said other ionized constituents and processing means electrically connected to said measuring means for computing a quantity of ammonia in said test sample based upon said peak ion current generated by said clusters and measured by said ion current measurement means.

16. The ion mobility spectrometer according to claim 15, wherein said ester dopant comprises an ester of phosphoric acid.

17. The ion mobility spectrometer according to claim 16, wherein said ester of phosphoric acid is a phosphonate.

18. The ion mobility spectrometer according to claim 17, wherein said phosphonate is dimethyl methyl phosphonate (DMMP).

19. The ion mobility spectrometer according to claim 15, wherein said doping means for applying an ester dopant to said test sample further comprises a permeation tube in fluid communication with said inlet region for introducing DMMP permeating through said tube.

20. The ion mobility spectrometer according to claim 19, wherein said permeation tube introduces said ester dopant to said inlet region at a rate of about 365 nanograms per minute.

21. The ion mobility spectrometer according to claim 19, wherein said permeation tube comprises means for maintaining a constant temperature of DMMP permeating through said tube for preserving a uniform rate of permeation.

22. The ion mobility spectrometer according to claim 21, wherein said means for maintaining a constant temperature is a thermostat.

23. The ion mobility spectrometer according to claim 19, wherein said permeation tube is immersed in a carrier gas stream of air used for carrying said test sample into said reaction region.

24. The ion mobility spectrometer according to claim 19, wherein said permeation tube is immersed in a drift gas stream of air which is applied to the drift region of said ion mobility spectrometer.

25. The apparatus according to claim 15, wherein said inlet region is partitioned by means for preventing passage of select constituents of said test sample.

26. The apparatus according to claim 25, wherein said partition means is a gas-permeable membrane.

27. The apparatus according to claim 26, wherein said gas-permeable membrane is a microporous material.

28. The apparatus according to claim 15, wherein said ion mobility spectrometer is operated in a positive ion mode.

29. The apparatus according to claim 15, wherein said processing means further comprises a memory for storing a look-up table of expected ammonia concentrations corresponding to said measured peak ion current data, said processing means comparing actual measured ion currents detected by said cell ion current detector to said expected ammonia concentrations.

30. The apparatus according to claim 29, wherein said processing means compares a moving average of said actual measured ion currents detected by said ion current detector to said expected ammonia concentrations.

* * * * *